(12) United States Patent
Heidmann et al.

(10) Patent No.: US 7,967,014 B2
(45) Date of Patent: *Jun. 28, 2011

(54) APPLICATION DEVICE FOR BREATHING MASK ARRANGEMENT

(75) Inventors: Dieter Heidmann, Berg (DE); Richard Brandmeier, Egling (DE); Stefan Madaus, Krailling (DE); Harald Voegele, Gauting (DE)

(73) Assignee: MAP Medizin-Technologie GmbH, Martinsried (DE)

( * ) Notice: Subject to any disclaimer, the term of this patent is extended or adjusted under 35 U.S.C. 154(b) by 427 days.

This patent is subject to a terminal disclaimer.

(21) Appl. No.: 11/410,252

(22) Filed: Apr. 25, 2006

(65) Prior Publication Data

US 2006/0191538 A1    Aug. 31, 2006

Related U.S. Application Data

(63) Continuation of application No. 10/277,091, filed on Oct. 22, 2002, now Pat. No. 7,059,326.

(30) Foreign Application Priority Data

Oct. 22, 2001   (DE) .................................. 101 51 984

(51) Int. Cl.
*A62B 18/08* (2006.01)

(52) U.S. Cl. .......... 128/207.11; 128/206.21; 128/205.25

(58) Field of Classification Search ............. 128/206.24, 128/207.11, 206.21, 206.26; 24/68 R
See application file for complete search history.

(56) References Cited

U.S. PATENT DOCUMENTS

| 781,516 A | 1/1905 | Guthrie |
| 812,706 A | 2/1906 | Warbasse |
| 1,081,745 A | 12/1913 | Johnston et al. |
| 1,176,886 A | 3/1916 | Ermold |
| 1,192,186 A | 7/1916 | Greene |
| 1,653,572 A | 12/1927 | Jackson |
| 1,926,027 A | 9/1933 | Biggs |
| 2,123,353 A | 7/1938 | Catt |

(Continued)

FOREIGN PATENT DOCUMENTS

AU         91/77110         11/1991

(Continued)

OTHER PUBLICATIONS

Decision Dated Dec. 6, 2007 (Received on Feb. 4, 2008); Opposition hearing by Weinmann . . . against German Patent 101 51 984 (including English Translation of the Decision).

(Continued)

*Primary Examiner* — Steven O Douglas
(74) *Attorney, Agent, or Firm* — Nixon & Vanderhye P.C.

(57) ABSTRACT

An application device for a breathing mask arrangement includes a base portion, a holding portion structured to support a mask and pivotally mounted to the base portion for pivotal movement about a first pivot axis, a right arm element pivotally mounted to the base portion for pivotal movement about a second pivot axis, and a left arm element pivotally mounted to the base portion for pivotal movement about a third pivot axis. The right and left arm elements are each provided with a contact portion for bearing against a right and a left forehead zone respectively of a mask user. The holding portion, the right arm element, and left arm element can be pivoted with respect to the base portion about the respective first, second, and third pivot axes.

19 Claims, 8 Drawing Sheets

U.S. PATENT DOCUMENTS

| | | | |
|---|---|---|---|
| 2,245,658 A | 6/1941 | Erickson | |
| 2,245,969 A | 6/1941 | Francisco et al. | |
| 2,248,477 A | 7/1941 | Lombard | |
| 2,254,854 A | 9/1941 | O'Connell | |
| 2,317,608 A | 4/1943 | Heidbrink | |
| 2,371,965 A | 3/1945 | Lehmberg | |
| 2,376,871 A | 5/1945 | Fink | |
| 2,415,846 A | 2/1947 | Randall | |
| 2,438,058 A | 3/1948 | Kincheloe | |
| 2,578,621 A | 12/1951 | Yant | |
| 2,590,006 A | 3/1952 | Gordon | |
| 2,820,651 A * | 1/1958 | Phillips | 285/127.1 |
| 2,931,356 A | 4/1960 | Schwarz | |
| D188,084 S | 5/1960 | Garelick | |
| 2,939,458 A | 6/1960 | Lundquist | |
| 3,013,556 A | 12/1961 | Galleher | |
| 3,182,659 A | 5/1965 | Blount et al. | |
| 3,189,027 A | 6/1965 | Bartlett | |
| 3,193,624 A | 7/1965 | Webb et al. | |
| 3,238,943 A | 3/1966 | Holley | |
| 3,315,674 A | 4/1967 | Bloom et al. | |
| 3,330,273 A | 7/1967 | Bennett | |
| 3,362,420 A | 1/1968 | Blackburn et al. | |
| 3,363,833 A | 1/1968 | Laerdal | |
| 3,556,122 A | 1/1971 | Laerdal | |
| 3,580,051 A | 5/1971 | Blevins | |
| 3,700,000 A | 10/1972 | Hesse et al. | |
| 3,720,235 A | 3/1973 | Schrock | |
| 3,750,333 A | 8/1973 | Vance | |
| 3,752,157 A | 8/1973 | Malmin | |
| 3,796,216 A | 3/1974 | Schwarz | |
| 3,799,164 A | 3/1974 | Rollins | |
| D231,803 S | 6/1974 | Huddy | |
| 3,830,230 A | 8/1974 | Chester | |
| 4,077,404 A | 3/1978 | Elam | |
| D250,131 S | 10/1978 | Lewis et al. | |
| 4,120,302 A | 10/1978 | Ziegler | |
| 4,167,185 A | 9/1979 | Lewis | |
| 4,226,234 A | 10/1980 | Gunderson | |
| 4,245,632 A | 1/1981 | Houston | |
| D262,322 S | 12/1981 | Mizerak | |
| 4,304,229 A | 12/1981 | Curtin | |
| 4,328,797 A | 5/1982 | Rollins et al. | |
| 4,347,205 A | 8/1982 | Stewart | |
| 4,354,488 A | 10/1982 | Bartos | |
| 4,402,316 A | 9/1983 | Gadberry | |
| 4,412,537 A | 11/1983 | Tiger | |
| 4,467,799 A | 8/1984 | Steinberg | |
| 4,522,639 A | 6/1985 | Ansite et al. | |
| 4,558,710 A | 12/1985 | Eichler | |
| D285,496 S | 9/1986 | Berman | |
| 4,616,647 A | 10/1986 | McCreadie | |
| 4,622,964 A | 11/1986 | Flynn | |
| 4,655,213 A | 4/1987 | Rapoport et al. | |
| 4,665,570 A | 5/1987 | Davis | |
| 4,671,271 A | 6/1987 | Bishop et al. | |
| 4,677,975 A | 7/1987 | Edgar et al. | |
| 4,677,977 A | 7/1987 | Wilcox | |
| H397 H | 1/1988 | Stark | |
| D293,613 S | 1/1988 | Wingler | |
| 4,739,755 A | 4/1988 | White et al. | |
| 4,770,169 A | 9/1988 | Schmoegner et al. | |
| 4,774,941 A | 10/1988 | Cook | |
| 4,782,832 A | 11/1988 | Trimble et al. | |
| 4,799,477 A | 1/1989 | Lewis | |
| 4,807,617 A | 2/1989 | Nesti | |
| 4,809,692 A | 3/1989 | Nowacki et al. | |
| 4,819,629 A | 4/1989 | Jonson | |
| 4,821,713 A | 4/1989 | Bauman | |
| 4,832,017 A * | 5/1989 | Schnoor | 128/206.12 |
| 4,841,953 A | 6/1989 | Dodrill | |
| 4,848,334 A | 7/1989 | Bellm | |
| 4,848,366 A | 7/1989 | Aita et al. | |
| 4,907,584 A | 3/1990 | McGinnis | |
| 4,910,806 A | 3/1990 | Baker et al. | |
| 4,919,128 A * | 4/1990 | Kopala et al. | 128/207.18 |
| 4,938,210 A | 7/1990 | Shene | |
| 4,938,212 A | 7/1990 | Snook et al. | |
| 4,944,310 A | 7/1990 | Sullivan | |
| D310,431 S | 9/1990 | Bellm | |
| 4,971,051 A | 11/1990 | Toffolon | |
| 4,986,269 A | 1/1991 | Hakkinen | |
| 4,989,596 A | 2/1991 | Macris et al. | |
| 4,989,599 A | 2/1991 | Carter | |
| 5,005,568 A | 4/1991 | Loescher et al. | |
| 5,005,571 A | 4/1991 | Dietz | |
| 5,027,809 A | 7/1991 | Robinson | |
| 5,038,776 A | 8/1991 | Harrison et al. | |
| 5,042,473 A | 8/1991 | Lewis | |
| 5,042,478 A | 8/1991 | Kopala et al. | |
| 5,046,200 A | 9/1991 | Feder | |
| 5,063,922 A | 11/1991 | Hakkinen | |
| 5,069,205 A | 12/1991 | Urso | |
| D323,908 S | 2/1992 | Hollister et al. | |
| 5,109,839 A | 5/1992 | Blasdell et al. | |
| 5,109,840 A | 5/1992 | Daleiden | |
| 5,121,745 A | 6/1992 | Israel | |
| 5,133,347 A | 7/1992 | Huennebeck | |
| 5,140,980 A | 8/1992 | Haughey et al. | |
| 5,140,982 A | 8/1992 | Bauman | |
| 5,159,938 A | 11/1992 | Laughlin | |
| 5,178,138 A | 1/1993 | Walstrom et al. | |
| D334,633 S | 4/1993 | Rudolph | |
| 5,220,699 A | 6/1993 | Farris | |
| 5,231,983 A | 8/1993 | Matson et al. | |
| 5,233,978 A | 8/1993 | Callaway | |
| 5,243,971 A | 9/1993 | Sullivan et al. | |
| 5,245,995 A | 9/1993 | Sullivan et al. | |
| 5,265,595 A | 11/1993 | Rudolph | |
| 5,279,289 A | 1/1994 | Kirk | |
| 5,280,784 A | 1/1994 | Kohler | |
| 5,311,862 A | 5/1994 | Blasdell et al. | |
| 5,322,057 A | 6/1994 | Raabe et al. | |
| 5,343,878 A | 9/1994 | Scarberry et al. | |
| 5,357,945 A * | 10/1994 | Messina | 128/200.14 |
| 5,357,951 A | 10/1994 | Ratner | |
| 5,372,130 A | 12/1994 | Stern et al. | |
| 5,388,571 A | 2/1995 | Roberts et al. | |
| 5,404,871 A | 4/1995 | Goodman et al. | |
| 5,419,318 A | 5/1995 | Tayebi | |
| 5,429,126 A | 7/1995 | Bracken | |
| 5,429,683 A | 7/1995 | Le Mitouard | |
| 5,431,158 A | 7/1995 | Tirotta | |
| 5,438,981 A | 8/1995 | Starr et al. | |
| 5,441,046 A | 8/1995 | Starr et al. | |
| D362,061 S | 9/1995 | McGinnis et al. | |
| 5,477,852 A | 12/1995 | Landis et al. | |
| 5,479,920 A | 1/1996 | Piper et al. | |
| 5,481,763 A | 1/1996 | Brostrom et al. | |
| 5,488,948 A | 2/1996 | Dubruille et al. | |
| 5,492,116 A | 2/1996 | Scarberry et al. | |
| 5,501,214 A | 3/1996 | Sabo | |
| 5,509,404 A | 4/1996 | Lloyd et al. | |
| 5,517,986 A | 5/1996 | Starr et al. | |
| 5,538,000 A | 7/1996 | Rudolph | |
| 5,540,223 A | 7/1996 | Starr et al. | |
| 5,542,128 A | 8/1996 | Lomas | |
| 5,546,936 A | 8/1996 | Virag et al. | |
| 5,558,090 A * | 9/1996 | James | 128/207.18 |
| RE35,339 E | 10/1996 | Rapoport | |
| 5,560,354 A | 10/1996 | Berthon-Jones et al. | |
| 5,570,682 A | 11/1996 | Johnson | |
| 5,570,689 A | 11/1996 | Starr et al. | |
| D377,089 S | 12/1996 | Starr et al. | |
| 5,592,938 A | 1/1997 | Scarberry et al. | |
| 5,608,647 A | 3/1997 | Rubsamen et al. | |
| 5,642,730 A | 7/1997 | Baran | |
| 5,647,355 A | 7/1997 | Starr et al. | |
| 5,647,357 A | 7/1997 | Barnett et al. | |
| 5,649,532 A | 7/1997 | Griffiths | |
| 5,649,533 A | 7/1997 | Oren | |
| 5,655,520 A | 8/1997 | Howe et al. | |
| 5,655,527 A | 8/1997 | Scarberry et al. | |
| 5,657,493 A | 8/1997 | Ferrero et al. | |
| 5,657,752 A * | 8/1997 | Landis et al. | 128/207.13 |
| 5,662,101 A | 9/1997 | Ogden et al. | |
| 5,666,946 A | 9/1997 | Langenback | |

| Patent Number | Kind | Date | Inventor |
|---|---|---|---|
| 5,685,296 | A | 11/1997 | Zdrojkowski et al. |
| 5,687,715 | A | 11/1997 | Landis et al. |
| 5,715,814 | A | 2/1998 | Ebers |
| 5,724,965 | A | 3/1998 | Handke et al. |
| 5,746,201 | A | 5/1998 | Kidd |
| 5,813,423 | A | 9/1998 | Kirchgeorg |
| 5,832,918 | A | 11/1998 | Pantino |
| D402,755 | S | 12/1998 | Kwok |
| 5,921,239 | A | 7/1999 | McCall et al. |
| 5,937,851 | A | 8/1999 | Serowski et al. |
| D423,096 | S | 4/2000 | Kwok |
| 6,044,844 | A | 4/2000 | Kwok et al. |
| D428,987 | S | 8/2000 | Kwok |
| 6,098,205 | A | 8/2000 | Schwartz et al. |
| 6,112,746 | A | 9/2000 | Kwok et al. |
| 6,119,693 | A * | 9/2000 | Kwok et al. ............ 128/207.11 |
| 6,123,071 | A | 9/2000 | Berthon-Jones et al. |
| 6,152,137 | A | 11/2000 | Schwartz et al. |
| D439,326 | S | 3/2001 | Hecker et al. |
| 6,196,223 | B1 * | 3/2001 | Belfer et al. ............ 128/206.25 |
| D443,355 | S | 6/2001 | Gunaratnam et al. |
| 6,257,237 | B1 | 7/2001 | Suzuki |
| 6,341,606 | B1 | 1/2002 | Bordewick et al. |
| 6,388,640 | B1 * | 5/2002 | Chigira et al. .................... 345/8 |
| 6,397,847 | B1 | 6/2002 | Scarberry et al. |
| 6,427,694 | B1 * | 8/2002 | Hecker et al. ............ 128/206.21 |
| 6,463,931 | B1 * | 10/2002 | Kwok et al. ............ 128/207.11 |
| 6,467,483 | B1 * | 10/2002 | Kopacko et al. ......... 128/207.12 |
| D468,823 | S | 1/2003 | Smart |
| 6,520,182 | B1 * | 2/2003 | Gunaratnam ............ 128/206.27 |
| 6,532,961 | B1 * | 3/2003 | Kwok et al. ............ 128/206.21 |
| 6,557,556 | B2 | 5/2003 | Kwok |
| 6,595,214 | B1 * | 7/2003 | Hecker et al. ............ 128/207.13 |
| 6,631,718 | B1 | 10/2003 | Lovell |
| D484,237 | S | 12/2003 | Lang et al. |
| 6,679,261 | B2 | 1/2004 | Lithgow |
| 6,691,707 | B1 | 2/2004 | Gunaratnam et al. |
| 6,691,708 | B2 | 2/2004 | Kwok et al. |
| 6,712,072 | B1 * | 3/2004 | Lang ....................... 128/206.27 |
| D492,992 | S | 7/2004 | Guney et al. |
| 7,059,326 | B2 * | 6/2006 | Heidmann et al. ....... 128/207.11 |
| 7,100,610 | B2 | 9/2006 | Biener et al. |
| 7,219,670 | B2 * | 5/2007 | Jones et al. ............. 128/206.27 |
| 2003/0019496 | A1 | 1/2003 | Kopacko et al. |
| 2003/0034034 | A1 | 2/2003 | Kwok et al. |
| 2003/0062048 | A1 | 4/2003 | Gradon |
| 2003/0075180 | A1 * | 4/2003 | Raje et al. ................ 128/206.24 |
| 2003/0075182 | A1 | 4/2003 | Heidmann et al. |
| 2003/0089373 | A1 | 5/2003 | Gradon |
| 2003/0115662 | A1 * | 6/2003 | Dobbie et al. ..................... 2/422 |
| 2003/0221691 | A1 | 12/2003 | Biener et al. |
| 2004/0045550 | A1 | 3/2004 | Lang et al. |
| 2004/0045551 | A1 | 3/2004 | Eaton |
| 2004/0177850 | A1 | 9/2004 | Gradon |

FOREIGN PATENT DOCUMENTS

| | | |
|---|---|---|
| AU | 94/64816 | 12/1994 |
| AU | 95/16178 B | 7/1995 |
| AU | 9459430 | 2/1996 |
| AU | A 32914/95 | 2/1996 |
| AU | A 41018/97 | 4/1998 |
| AU | A 89312/98 | 1/1999 |
| CA | 1039144 | 9/1928 |
| DE | 284 800 C | 11/1913 |
| DE | 284800 A | 11/1913 |
| DE | 459104 | 4/1928 |
| DE | 701 690 | 1/1941 |
| DE | 159396 | 6/1981 |
| DE | 3015279 | 10/1981 |
| DE | 3345067 | 6/1984 |
| DE | 3537507 | 4/1987 |
| DE | 3539073 | 5/1987 |
| DE | 4004157 | 4/1991 |
| DE | 4343205 | 6/1995 |
| DE | 29715718 | 10/1997 |
| DE | 19735359 | 1/1998 |
| DE | 29723101 | 7/1998 |
| DE | 29810846 U1 | 8/1998 |
| DE | 198 17 332 | 1/1999 |
| DE | 198 17 332 A1 | 1/1999 |
| DE | 198 08 105 | 9/1999 |
| DE | 198 08 105 A1 | 9/1999 |
| DE | 20005346 | 5/2000 |
| DE | 29923141 U | 5/2000 |
| DE | 20017940 A | 10/2000 |
| DE | 200 17 940 | 12/2000 |
| DE | 199 54 517 | 6/2001 |
| DE | 199 54 517 A1 | 6/2001 |
| DE | 10045183 | 5/2002 |
| EP | 0 054 154 | 10/1981 |
| EP | 0 0252 052 | 1/1988 |
| EP | 0 264 772 | 4/1988 |
| EP | 0 386 605 | 2/1990 |
| EP | 0427474 | 5/1991 |
| EP | 0 462 701 | 12/1991 |
| EP | 0 602 424 | 11/1993 |
| EP | 0 608 684 | 8/1994 |
| EP | 00697225 | 7/1995 |
| EP | 178925 A2 | 4/1996 |
| EP | 0 747 078 | 12/1996 |
| EP | 0821978 | 2/1998 |
| EP | 1099452 | 5/2001 |
| EP | 1205205 | 11/2001 |
| FR | 2 574 657 | 6/1986 |
| FR | 2 658 725 | 8/1991 |
| FR | 2749176 | 12/1997 |
| GB | 1395391 | 5/1975 |
| GB | 1467828 | 3/1977 |
| GB | 2145335 | 3/1985 |
| GB | 2147506 | 5/1985 |
| GB | 2 164 569 | 3/1986 |
| GB | 2 186 801 | 8/1987 |
| GB | 2 267 648 | 12/1993 |
| JP | 09/216240 | 8/1997 |
| JP | 11-000397 | 1/1999 |
| JP | 2000-225191 | 8/2000 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 9812965 | 4/1998 |
| WO | WO 98/18514 | 5/1998 |
| WO | WO/98/24499 | 6/1998 |
| WO | WO 98/26829 | 6/1998 |
| WO | WO 98/26830 | 6/1998 |
| WO | WO 9834665 | 8/1998 |
| WO | WO 98/48878 | 11/1998 |
| WO | WO 9943375 | 9/1999 |
| WO | WO99/58181 | 11/1999 |
| WO | WO 99/58181 | 11/1999 |
| WO | WO 99/65554 | 12/1999 |
| WO | WO 00/21600 | 4/2000 |
| WO | WO 00/57942 | 10/2000 |
| WO | WO 00/69521 | 11/2000 |
| WO | WO 00/78384 | 12/2000 |
| WO | WO 0078381 | 12/2000 |
| WO | WO 0078384 | 12/2000 |
| WO | WO 01/97892 | 12/2001 |
| WO | WO 02/32491 * | 4/2002 |
| WO | WO 03/059427 | 7/2003 |
| WO | WO 2004/022145 | 3/2004 |

| | | |
|---|---|---|
| WO | WO 2004022144 | 3/2004 |
| WO | WO 2004022145 | 3/2004 |
| WO | WO 2004/078228 | 9/2004 |

OTHER PUBLICATIONS

Various invoices relating to the "Somnomask," as well as a brochure of the model "Somnomask" of 1999.

Translation of Office Action issued in Japanese Patent Appln. No. 2003-559587 mailed Mar. 17, 2009.

European Search Report issued in Appln. No. EP 02714190.2 (Jul. 11, 2006).

Mask 1 Photographs, Respironics Inc., Reusable Full Mask (small), Part #452033, Lot #951108.

Mask 2 Photographs, Puritan—Bennett, Adam Circuit, Shell Part #231700, Swivel Part #616329-00, Pillows (medium), Part #616324.

Mask 3 Photographs, DeVilbiss Healthcare Inc., Devilbiss Seal-Ring and CPAPMask Kit (medium), Part #73510-669.

Mask 4 Photographs, Respironics Inc., Monarch Mini Mask with Pressure Port, Part #572004, Monarch Headgear, Part #572011.

Mask 5 Photographs, Healthdyne Technologies, Nasal CPAP Mask (medium narrow), Part #702510.

Mask 6 Photographs, Healthdyne Technologies, Soft Series Nasal CPAP Mask, Part #702020.

Mask 7 Photographs, DeVilbiss Healthcare Inc., Small Mask and Seal Rings, Part #73510-668.

Mask 8 Photographs, Respironics Inc., Reusable Contour Mask (medium), Part #302180.

Mask 9 Photographs, Healthdyne Technologies, Healthdyne Large Headgear.

Mask 10 Photographs, Respironics Inc., Soft Cap (medium), Part #302142.

Mask 11 Photographs, Weinmann: Hamburg, Nasalmaskensystem mit Schalldämpfer (medium), Part #WN 23105.

Mask 12 Photographs, Life Care.

Mask 13 Photographs, Healthdyne Technologies.

Mask 14 Photographs, King System.

Mask 15 Photographs, Respironics Inc., Pediatric Mask.

Mask 16 Photographs, Hans Rudolph Inc., Hans Rudolph Silicone Rubber Face Mask/8900.

Photograph of Weinmann Mask, acquired prior to 1998.

Somotron CPAP-Great WM 2300 Instruction Manual, Weinmann Hamburg, 11 pgs, 1991.

9 photographs of Weinmann mask, WM 23122 !991.

The ResMed Range of Mask Systems, product brochure, Nov. 1995, 4 pgs.

Product Brochure for ResMed "Sullivan® Mirage™—The Mirage is Real. A Perfect Fit—First Time," ©1997 ResMed Limited, 4 pages.

Product Brochure for ResMed "Sullivan® Mirage™—The Mirage is Real. A Perfect Fit—First Time," © 1998 ResMed Limited, 4 pages.

U.S. Appl. No. 11/630,360, filed Dec. 2006, Hitchcock et al.

* cited by examiner

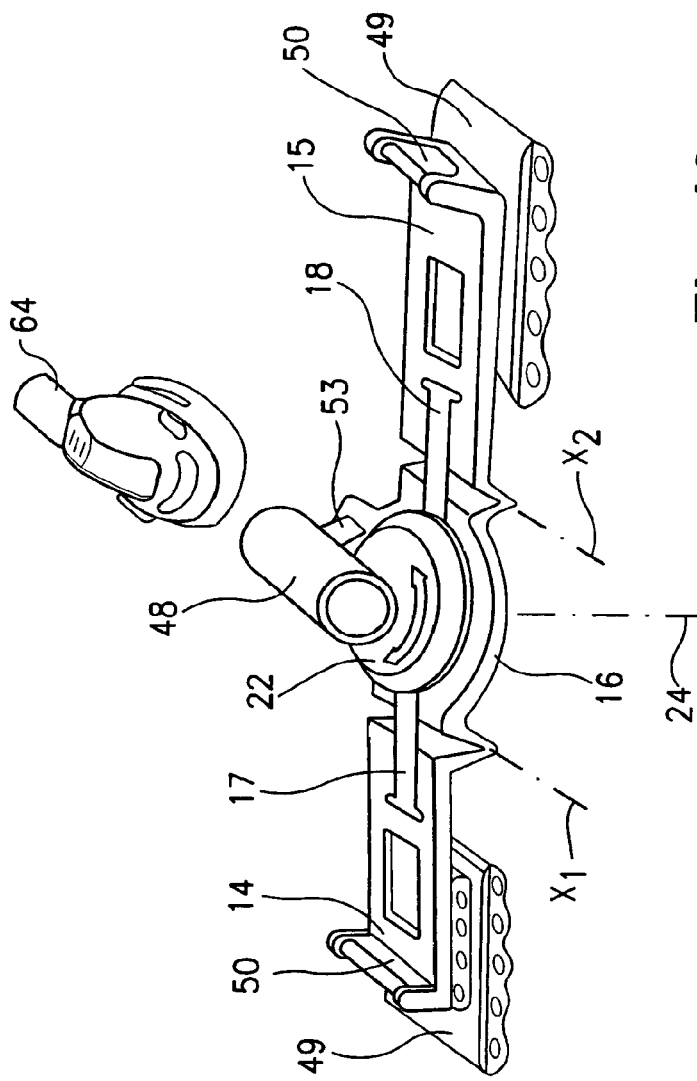
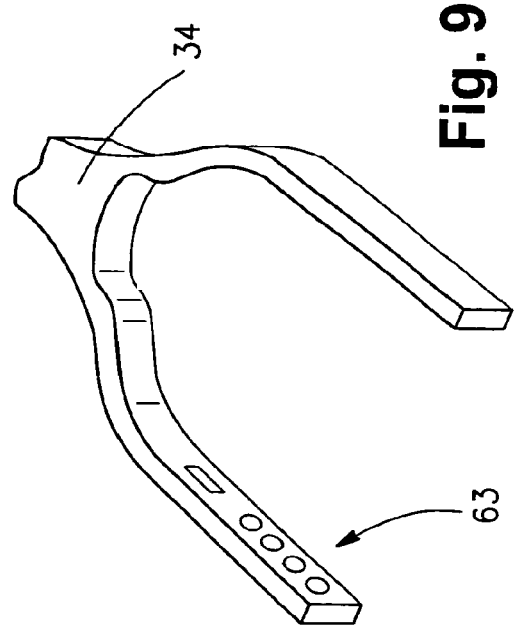
Fig. 10
Fig. 9

APPLICATION DEVICE FOR BREATHING MASK ARRANGEMENT

This application is a continuation of U.S. application Ser. No. 10/277,091, filed Oct. 22, 2002, now U.S. Pat. No. 7,059,326, which is incorporated herein by reference in its entirety.

FIELD OF THE INVENTION

The invention relates to an application device for a breathing mask arrangement as can be used, for example, in the context of CPAP-therapy for treating sleep-related respiratory disturbances.

BACKGROUND OF THE INVENTION

In the context of what is referred to as CPAP-therapy, a patient can be supplied by way of a breathing mask arrangement with a breathable gas, in particular ambient air, at a pressure level which is above the ambient pressure. The increased pressure which is applied by the respiratory gas makes it possible to provide for pneumatic splinting of the respiratory tracts and thus to obviate any obstructions. In that connection the breathing mask arrangement is worn by the patient over the entire sleep or rest phase of the patient. The breathing mask arrangement is usually supported by way of a sealing lip zone in the region around the nose of the person using the mask and by way of a forehead support device in the forehead region of the mask user. The holding forces required to apply the breathing mask arrangement can be afforded by a fixing device which for example has a headband which is passed around the back of the head of the mask user. Under some circumstances, in the region in which the sealing lip device is applied and in the contact region of the forehead support device, surface pressures can occur, which result in the level of comfort involved in wearing the breathing mask arrangement being seriously adversely affected.

SUMMARY OF THE INVENTION

One aspect of the present invention is to provide an application device for a breathing mask arrangement, by which a breathing mask arrangement can be reliably held in the application position and which provides more comfort to the patient.

Another aspect of the invention provides an application device for a breathing mask arrangement. The application device according to one embodiment includes a forehead support device, wherein the forehead support device has a right arm element and a left arm element and the arm elements are provided with a contact portion provided for bearing against a left and right forehead zone respectively and each of the arm elements is arranged pivotably movably about a pivot axis.

The application device allows the breathing mask arrangement to be supported in the forehead region of the mask user by way of a forehead support device which can advantageously be adapted to different facial architectures.

Another aspect of the invention provides an adjusting drive device for deflection of the arm elements into a predetermined pivotal position. The adjusting drive device according to one embodiment is designed such that both arm elements are pivotable by way of the adjusting drive device simultaneously, that is to say at the same time. The adjusting drive device may include for example an adjusting wheel which, by way of a screw or spiral drive, is in engagement with actuating members which are displaceable radially with respect to an axis of rotation of the pivot wheel.

According to one embodiment, the pivot axes of each of arm elements are directed such that viewed in the application position in a front view, they extend transversely, e.g., substantially perpendicular, with respect to a transverse line joining the eyebrows. That advantageously makes it possible for the forehead support device to be precisely adapted to the curvature of the forehead of the user of the mask and thereby to precisely set the breathing mask which is held by the application device in the region of the contact zone of the sealing lip device, which contact zone crosses over the bridge of the nose.

According to another aspect of the present invention, each of the arm elements is pivotable about its own pivot axis associated therewith, wherein the pivot axes of the two arm members are spaced from each other at the level of a transverse line joining the eyebrows. According to one embodiment, the spacing of two pivot axes of the arm members is between 10 and 50 mm at the level of the transverse line joining the eyebrows. The length of the arm members is between about 25 and 75 mm depending on the respective spacing of the pivot axes.

According to another aspect of the present invention, adaptability of the forehead support device to the individual curvature of the forehead of the user of the mask can be further increased if the pivot axes of the arm members are inclined relative to each other through an angle α in the range of 8 and 45° relative to each other. In one embodiment, the structure defining the pivot axes can be designed in such a way that the angle α of the pivot axes relative to each other is adjustably variable.

In one embodiment, the pivot axes are established in such a way that, in relation to a front view of a user of the mask, they intersect in the region between the transverse line joining the eyebrows and the chin of the user of the mask. That affords particularly good compatibility in relation to the facial architectures which statistically predominantly prevail.

In one embodiment, the pivot axes are each defined by a respective hinge device. The hinge devices can be, e.g., in the form of multi-part pivot arrangements or film hinges. In one embodiment, the arm members and the hinge basic structures provided for pivotably mounting the arm members are produced in one piece from a plastic material, for example. Alternatively, the arm members and the hinge basic structures may be integrally connected with one another.

In accordance with another aspect of the present invention, the adjusting drive device according to one embodiment includes an adjusting wheel which is coupled by way of a spiral structure to actuating members. Thus, the arm elements can be deflected into defined pivotal positions. In one embodiment, the adjusting wheel is mounted rotatably about an axis which in the application position of the application device is oriented substantially perpendicularly to the surface of the forehead of the patient. The adjusting wheel of one embodiment has a diameter in the range of 20 and 50 mm and in the outside peripheral region it is provided with a profiling, e.g., a fluted or grooved structure, which permits the reliable transmission of the finger forces for rotating the adjusting wheel. The adjusting wheel according to one embodiment is arranged in an intermediate region between a respiratory gas conduit portion of the breathing mask arrangement and a base portion of the forehead support device. In that case it is possible for the finger forces for rotating the adjusting wheel to be applied by way of the thumb and the index finger, for example, in which case the respiratory gas conduit associated with the breathing mask arrangement is embraced by the fingers, by using the thumb and the index finger.

In accordance with a further aspect of the invention, an application device according to one embodiment for a breathing mask arrangement has a forehead support device, wherein the forehead support device has a right arm element and a left arm element and both arm elements are pivotably movably coupled to a breathing mask by way of a pivot axis, wherein the pivot axes extend substantially parallel to a transverse line which in the application position of the breathing mask arrangement joins the eyebrows of a user of the mask and there is provided an adjusting drive device for establishing the pivotal position of the arm elements.

The forehead support device may be used to adjust the contact pressure of a zone of the sealing lip device, which passes across the bridge of the nose of a user of the mask.

Further aspects, features, and advantages of the present invention will be apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 9 shows a perspective view of an embodiment of a holding portion of an application device, which is provided for coupling to a breathing mask arrangement, and FIG. 10 shows a perspective view of an embodiment of an application device for a breathing mask arrangement as can be fitted for example onto a respiratory gas conduit portion of a breathing mask.

DETAILED DESCRIPTION OF ILLUSTRATED EMBODIMENTS

Figure 1:
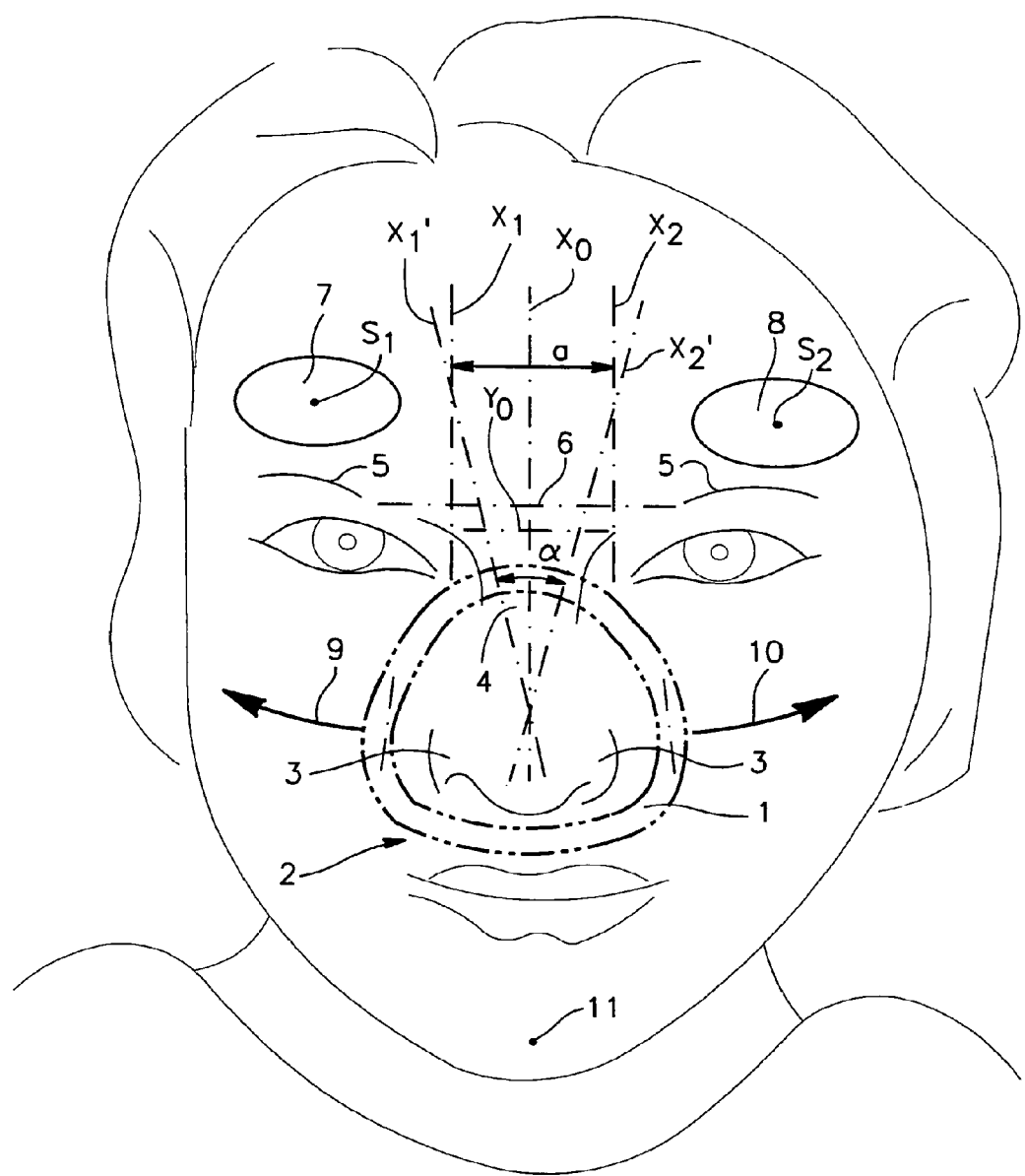
FIG. 1 shows a front view of the face region of a person to illustrate contact zones of a forehead support device and orientations of the pivot axes of pivotally mounted arm elements.

FIG. 1 shows a front view illustrating the surface of the face of a user of a breathing mask arrangement. For application or fitting of a breathing mask arrangement it is applied for example to the face of the mask user in such a way that a sealing lip contact zone 1 defined by a sealing lip device of the breathing mask arrangement and the surface of the face of the mask user, starting from the upper lip region 2, extends around the nostrils 3 to the bridge of the nose 4 and, e.g., passes across same at the level of the eyes.

The breathing mask arrangement according to one embodiment is supported on the forehead region of the mask user by way of a forehead support device which will be described in greater detail hereinafter. As shown in FIG. 1, support on the forehead region is implemented by way of two contact zones 7, 8 which are disposed above a transverse line 6 which joins the eyebrows 5. In the view illustrated, support for the breathing mask arrangement in the forehead region is implemented at two contact zones 7, 8, wherein the spacing of the centroids $S_1$, $S_2$ of the contact zones 7, 8 approximately corresponds to the spacing between the eyes of the mask user. However, the spacing of the centroids $S_1$, $S_2$ of the contact zones 7, 8 may be greater than or less than the spacing between the eyes of the mask user. In the illustrated embodiment, the contact pressure of the sealing lip device of the breathing mask arrangement in the region of the sealing lip contact zone 1 is adjustably variable by contact elements that are pivotable about pivot axes $X_0$, $X_1$, $X_1'$, $X_2$, $X_2'$ and about a transverse axis $Y_0$.

Support for the breathing mask arrangement on the face of the mask user can be implemented by the application device which is described in greater detail hereinafter, in such a way that the breathing mask arrangement and the forehead support device are supported on the face of the mask user substantially at three mutually spaced zones. In the forehead region in that case the forehead support device is supported at the contact zones 7, 8. The breathing mask arrangement is supported on the face of the mask user by way of the sealing lip contact zone 1. The fact that the application device and the breathing mask arrangement are supported on the face of the mask user at three main supporting zones advantageously provides that the breathing mask is supported in a statically defined manner. In one embodiment, the holding forces for holding the forehead support device in the forehead region are applied by way of an upper headband arrangement. For fixing the breathing mask arrangement in the nose region, a lower belt arrangement is provided, by way of which the breathing mask arrangement is urged against the surface of the face of the mask user by pulling forces 9 and 10 which act thereon at both sides and which are directed laterally relative to the cheeks. In one embodiment, the pulling forces 9, 10 are applied by a lower belt arrangement which is passed around the region of the back of the head of the mask user.

In the illustrated embodiment, the pivot axes $X_0$, $X_1$, $X_1'$, $X_2$, $X_2'$ which permit adjustment of the support configuration of the forehead support device extend away from the forehead region towards the upper lip region 2 of the user of the mask. The axes $X_1$, $X_2$ shown in FIG. 1 are oriented in mutually parallel relationship and spaced from each other by a spacing a which substantially corresponds to the width of the bridge of the nose, in particular the width of the bridge of the nose in the region of the tear duct openings of the mask user.

The pivot axes $X_1'$, $X_2'$ shown in FIG. 1 which are inclined relative to each other are also spaced in the region of the width a of the bridge of the nose, at the level of the contact zones 7 and 8. The axes $X_1'$, $X_2'$ are inclined relative to each other at an angle α which is selected such that the two axes intersect in the region between the base of the nose and the chin 11 of the mask user.

Figures 2, 2B:
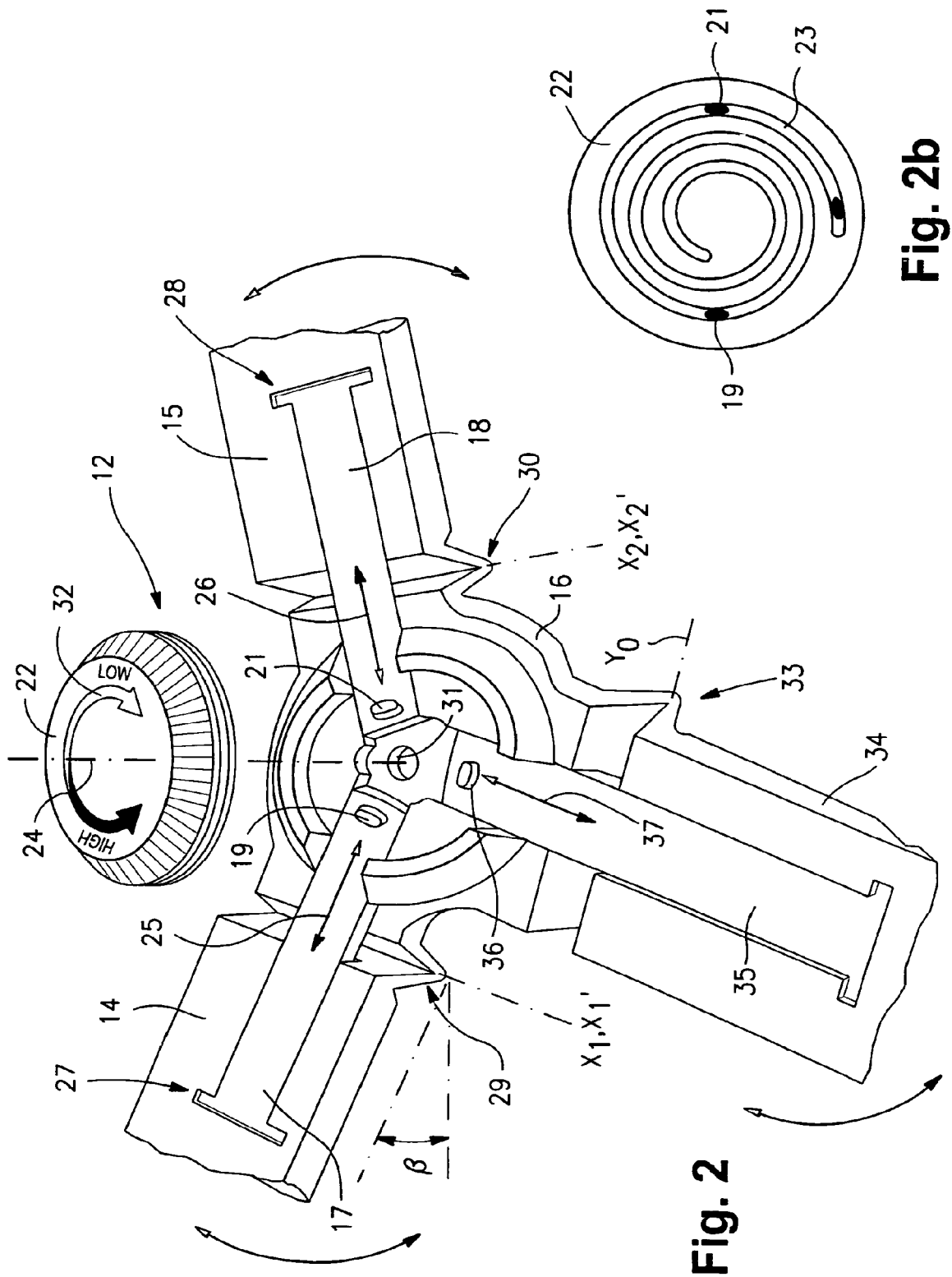
FIG. 2 is a perspective view illustrating an embodiment of an adjusting drive device for adjustably pivoting the arm elements.
FIG. 2B is a bottom view an adjusting wheel of the adjusting drive device shown in FIG. 2.

FIG. 2 is a perspective view that shows an embodiment of an adjusting drive 12, by way of which the pivotal position of a left arm element 14 and a right arm element 15 can be altered adjustably with respect to a base portion 16.

In this case the adjusting drive 12 includes a coupling member 17 associated with the left arm element 14 and a coupling member 18 associated with the right arm element 15.

In the illustrated embodiment, each of the two coupling members 17, 18 is provided with at least one engagement portion 19, 21 which is in engagement with an adjusting wheel 22 which is shown here in a position of having been lifted off, by way of a spiral structure 23 provided at the underside of the adjusting wheel 22 (see FIG. 2B). By rotating the adjusting wheel 22 about its axis of rotation 24, the engagement portions 19, 21, as indicated by the arrow symbols 25, 26, are displaced in the radial direction jointly with the coupling members 17, 18.

In the illustrated embodiment, the coupling members 17, 18 are coupled movably to the left and right arm elements 14, 15 respectively associated therewith. In the illustrated embodiment coupling of the coupling members 17, 18 to the arm elements 14, 15 associated therewith is effected in each case by way of a hinge portion 27 and 28 respectively which permits a pivotal movement of the coupling member 17, 18 with respect to the arm element 14, 15 associated therewith. The arm elements 14, 15 are coupled to the base portion 16 by way of a hinge connection 29, 30. The hinge connections 29, 30 are here in the form of film hinges. In this case the arm elements 14, 15 are formed integrally with the base portion 16. The hinge connections 29, 30 define the pivot axes $X_1$, $X_1'$ and $X_2$, $X_2'$ respectively referred to hereinbefore in connection with FIG. 1. As a consequence of the pair of forces applied to the respective arm element in the region of the hinge portions 27, 28 and the hinge connections 29, 30, the respective arm element can be moved with respect to the base portion 16 into a pivotal position which is defined by the radial spacing of the engagement portion 19, 21 from the axis of rotation 24. The maximum radial stroke movement of the engagement portions 19, 21 and the spatial position of the hinge portions and the hinge connections 27, 28 29, 30 are so selected that, for example in a range of rotary movement of the adjusting wheel 22 through an angle of rotation of 540°, it is possible to adjust a pivot angle β of the arm elements, 14, 15 in the range of 0 to 40°.

The arm elements 14, 15 may be movably connected to the base portion 16 in any other known manner to allow relative movement between the arm elements 14, 15 and the base portion 16. For example, the arm elements 14, 15 may be slidably connected to the base portion 16 or the arm elements 14, 15 may be connected to the base portion 16 such that the arm elements 14, 15 may bend with respect to the base portion 16.

In the illustrated embodiment, the adjusting wheel 22 is made from a plastic material and fitted by way of a central rotary trunnion or projection (not shown) into a bore 31 provided in the base portion 16. The adjusting wheel 22 has a diameter in the range of 35 to 55 mm, preferably 45 mm, and on its outside it is provided with a marking 32 which indicates the adjusting effect achieved by rotating the adjusting wheel 22.

In the embodiment illustrated, the base portion 16 is coupled by way of a further hinge connection 33 to a holding portion 34. The hinge connection 33 illustrated defines the pivot axis $Y_0$ indicated in FIG. 1. The pivotal movement of the holding portion 34 with respect to the base portion 16 is effected in the same manner as described hereinbefore with respect to the left and right arm elements 14, 15 by way of a coupling member 35 which is in engagement with the adjusting wheel 22 by way of an engagement portion 36 and is movable in the radial direction with respect to the axis of rotation 24, as indicated by the arrow symbol 37. The holding portion 34 is connected to a mask base body portion of a breathing mask arrangement by way of an intermediate structure which is not shown in detail here.

Mounted to the left and right arm elements 14, 15 as will be described in greater detail hereinafter, are contact pads by way of which the arm elements 14, 15 bear against the contact zones 7, 8 (FIG. 1) of the mask user.

As will also be described in greater detail hereinafter, the arm elements 14, 15 can be pulled onto the forehead region of the mask user by way of an upper headband arrangement, for example.

Figure 3:
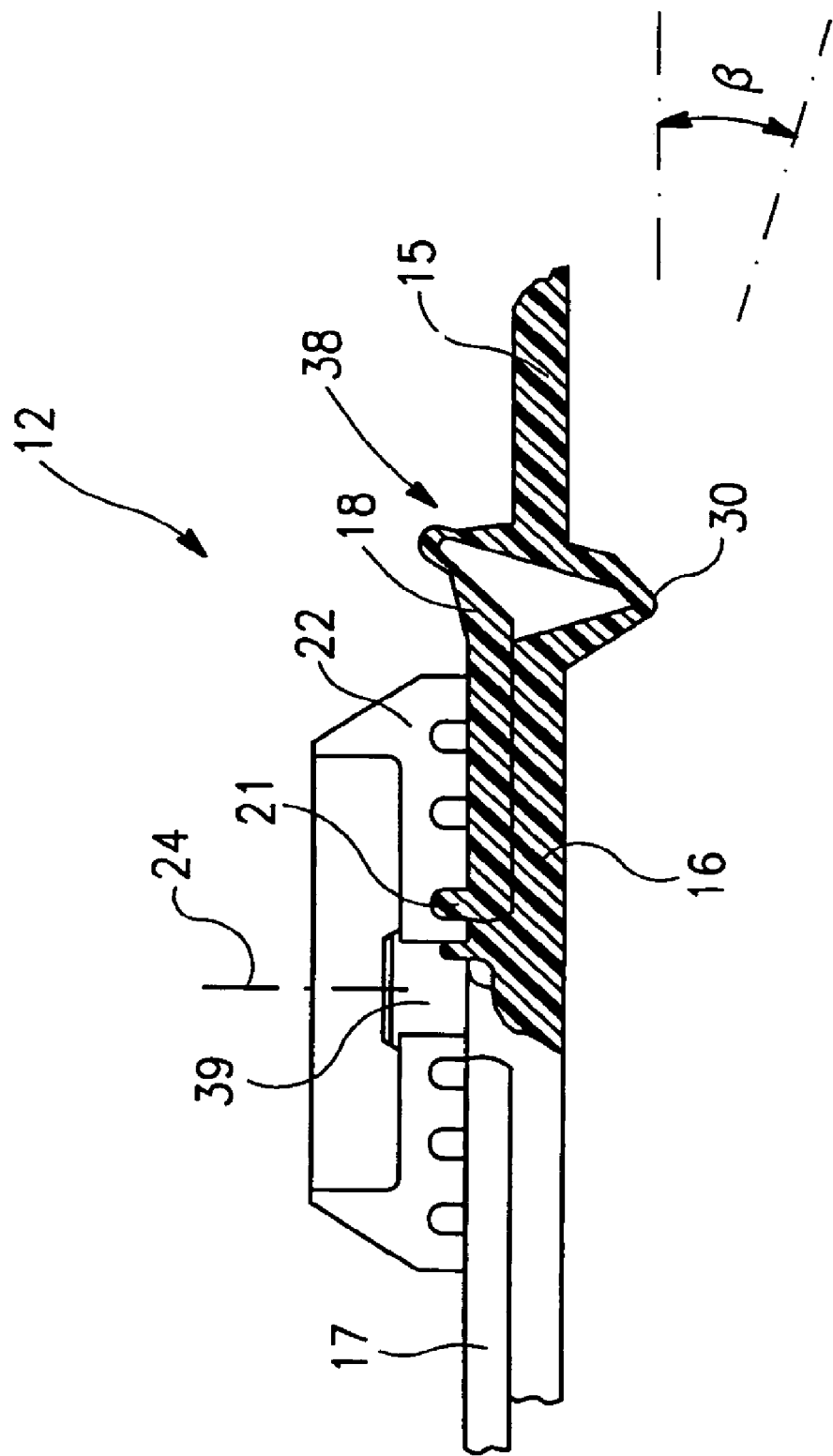
FIG. 3 shows a partial cross-sectional view to illustrate the structure of an embodiment of the adjusting drive, which is provided with film hinge structures.

FIG. 3 shows an embodiment of the adjusting drive 12 in which a coupling member 18 which is movable radially relative to the axis of rotation 24 of the adjusting wheel 22 is preferably formed in one piece with the arm element 15 associated therewith, in which case sufficient pivotal mobility is achieved by way of a film hinge structure 38. The base portion 16 is also preferably formed in one piece with the arm element 15 and is coupled thereto similarly to the embodiment shown in FIG. 2 by way of a hinge connection 30 which is also in the form of a film hinge. The portions at which forces are applied, as defined by the film hinge structure 38 and the hinge connection 30, are spaced from each other in such a way that, as a consequence of the radial stroke movement of the coupling member 18 which can be adjusted by the adjusting wheel 22, it is possible to achieve an adequate pivotal angle β of the arm element 15.

The adjusting wheel 22 is rotatably mounted on a rotary trunnion or projection 39 which stands up from the base portion 16. The underside of the adjusting wheel 22, which faces towards the base portion 16, has the spiral structures, like the above-described embodiment, which are in engagement with the engagement portion 21 provided integrally with the coupling member 18.

Figure 4:
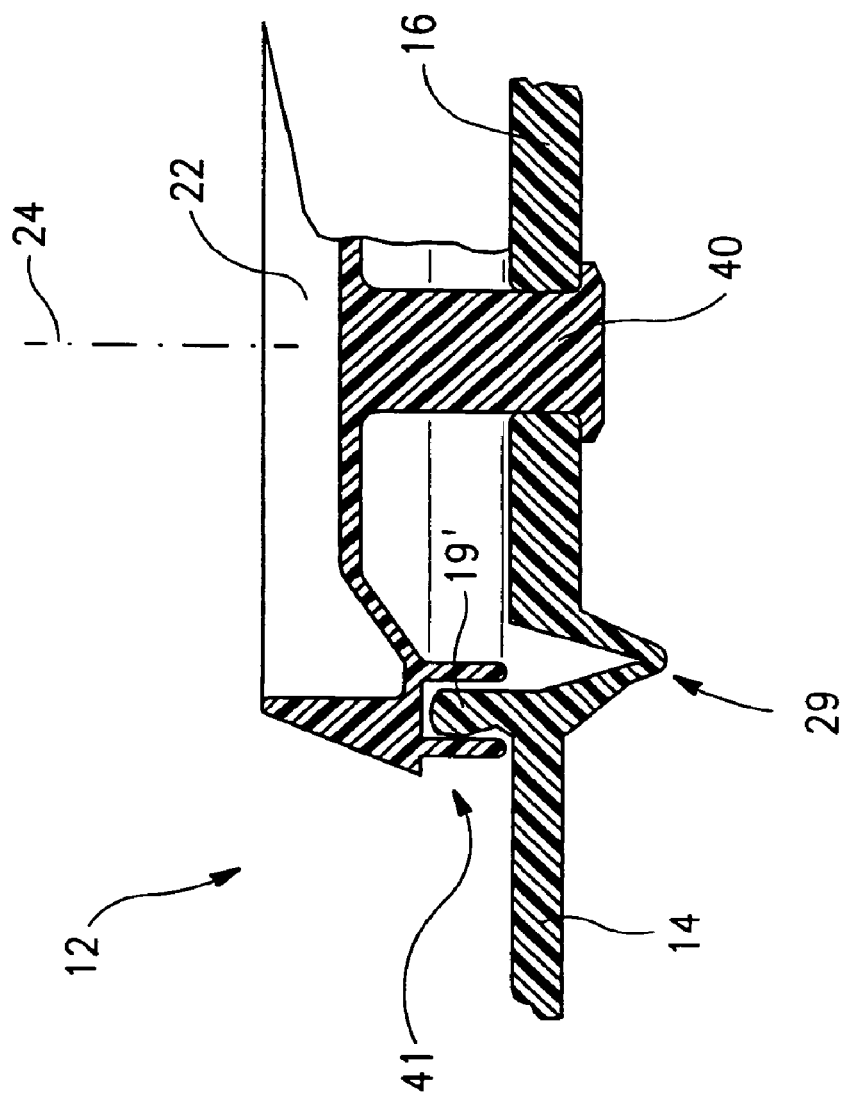
FIG. 4 shows a partial cross-sectional view to illustrate an embodiment of the adjusting drive device having a film hinge and a spiral groove region which is provided at an underside of the adjusting wheel and which is directly in engagement with an engagement portion of an arm element.

FIG. 4 illustrates another embodiment of the adjusting drive 12. In this embodiment, the adjusting drive 12 includes an adjusting wheel 22 coupled rotatably to the base portion 16 by way of a rotary trunnion or projection 40. Provided on the underside of the adjusting wheel 22, which faces towards the base portion 16, is a spiral structure 41 which is directly in engagement with an engagement portion 19' provided on the arm element 14. The arm element 14 is pivotably movably coupled to the base portion 16 by way of a hinge connection 29 which in this case also is in the form of a film hinge. Rotation of the adjusting wheel 22 about the axis of rotation 24 defined by the rotary trunnion 14 makes it possible to set different spacings of the engagement portion 19' from the axis of rotation 24, whereby the arm element 14 is pivotable with respect to the base portion 16 into respectively desired pivotal positions.

Figure 5:
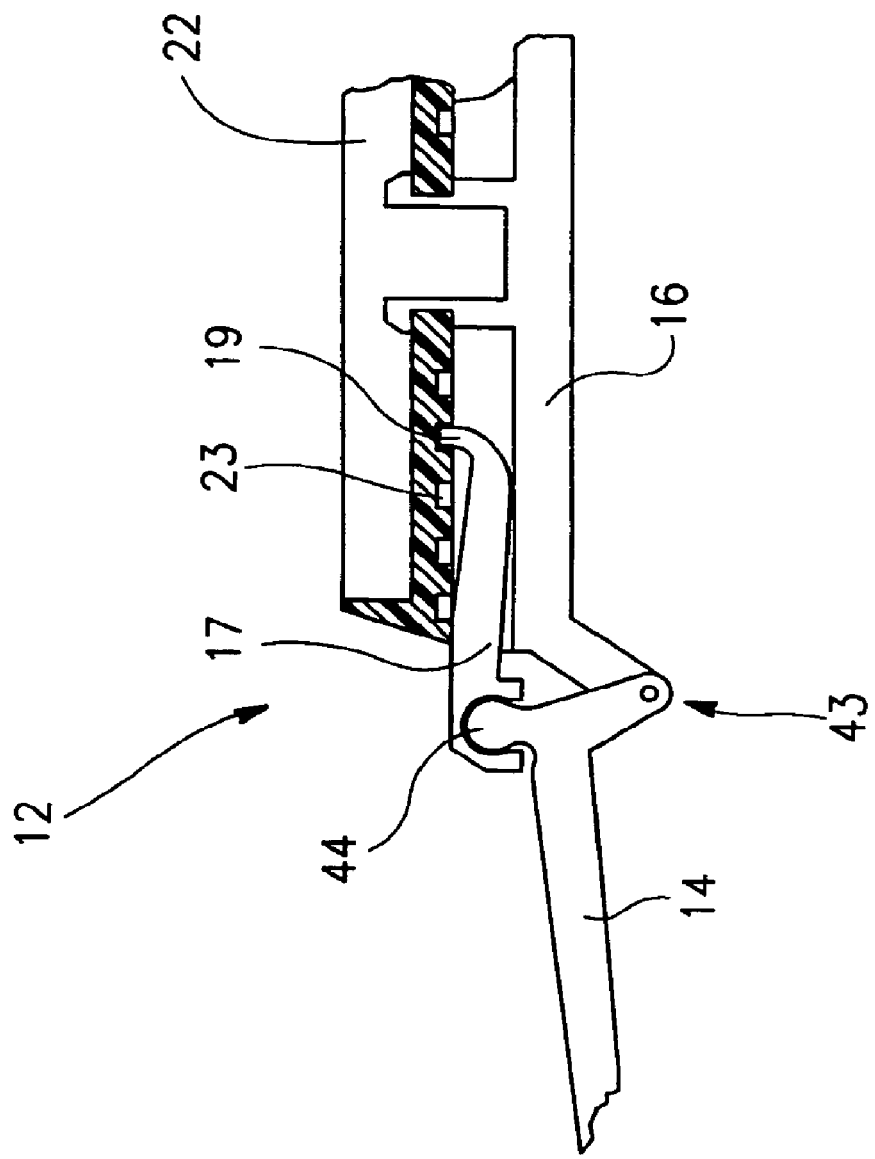
FIG. 5 shows a partial cross-sectional view of an embodiment of an adjusting drive device having an arm element which is mounted pivotably by way of a pivot pin zone.

FIG. 5 illustrates another embodiment of an adjusting drive 12, in which the base portion 16 and the arm element 14 are in the form of separate parts which are coupled together by way of a hinge device 43. Provided on the arm element 14 is a knob 44 to which the coupling member 17 is pivotably mounted. Similarly to the embodiments described hereinbefore, the coupling member 17 has an engagement portion 19 which is in engagement with the adjusting wheel 22 by way of a spiral structure 23. By rotation of the adjusting wheel 22, the coupling member 17 can be displaced in a defined manner in the radial direction and, in so doing, pivots the arm element about the hinge device 43 into a defined angular position with respect to the base portion 16. Braking structure may be provided, by which the adjusting wheel 22 can be sufficiently firmly fixed in a desired rotational position. Braking structure may be embodied, for example, by fine latching or detent projections which come into and out of engagement respectively in the course of relative movement of the components which are moved relative to each other, such movement being made by the inherent elasticity of the parts involved. The spiral structure 23 may be designed in such a way that it is substantially self-locking.

Figure 6:
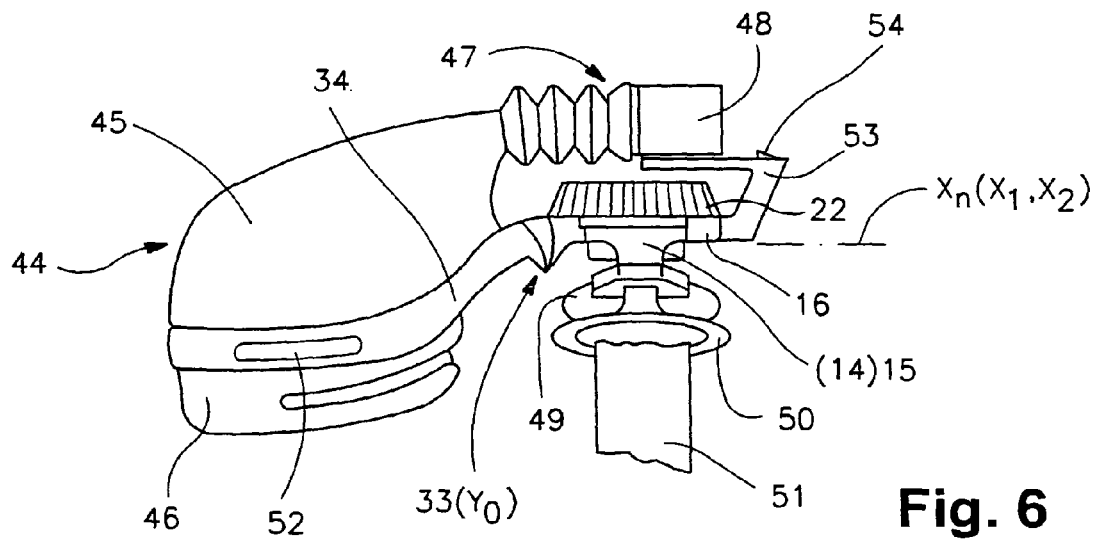
FIG. 6 shows a side view of an embodiment of an application device provided with a breathing mask arrangement.

FIG. 6 shows an application device according to one embodiment with a breathing mask arrangement 44 accommodated therein. The breathing mask arrangement 44 includes a mask base body 45 and a sealing lip device 46 which is coupled thereto. The sealing lip device 46 is made from an elastomer material, e.g., fully transparent silicone rubber, and in the application position sealingly contacts the sealing lip contact zone 1 of the mask user, as shown in FIG. 1. The feed of the respiratory gas into the interior of the mask which is defined by the mask base body 45 is effected by way of a flexible conduit portion 47 which in the illustrated embodiment is also made from an elastomer material and is in the form of a bellows structure. Connected to the flexible conduit portion is a breathing hose connecting portion 48 which has an inside diameter in the range of 12 and 35 mm. The breathing hose connecting portion 48 is coupled to the base portion 16 of the forehead support device. In the illustrated embodiment, the forehead support device 16 includes an adjusting wheel 22 disposed in an intermediate region between the flexible conduit portion 47 or the breathing hose connecting portion 48 and the base portion 16. The adjusting wheel 22 can be turned by the user of the mask by gripping around the flexible conduit portion 47, by way of the fingertips of the thumb and the index finger of the user of the mask, for example. Rotating the adjusting wheel 22 allows the arm elements 14 and 15 to be pivoted about the pivot axis $X_n$. As a result, a forehead pad 49 which is provided for making contact with the forehead region of the mask user can be adjustably positioned with respect to the base portion 16. Provided on the arm element 15 (14) is an eye portion 50, through which a portion of an upper headband arrangement 51 of a headband assembly 90 may pass (see FIGS. 6 and 7).

In the embodiment illustrated, the base portion 16 is pivotably movably connected to a holding portion 34 by way of the hinge connection 33. The holding portion 34 is of a frame-like configuration and embraces the mask base body 45 at least in the side region thereof. Also provided on the holding portion 34 are eye portions 52 through which a portion of a lower headband arrangement 91 of the headband assembly 90 can be passed (see FIG. 7). As an alternative to the design configuration involving the eye portions 52 or also in combination therewith, other coupling structures may be provided for coupling the holding portion 34 or the mask base body 45 to a headband arrangement.

Pivotal movement of the base portion 16 about the pivot axis $Y_0$ which is defined by the hinge connection 33 is effected in this embodiment simultaneously with the pivotal movement of the arm members 14, 15 about the axes $X_1$, $X_2$.

The breathing hose connecting portion 48 is coupled to the base portion 16. As shown in FIG. 6, coupling is effected by way of a holding foot 53 which is guided past the adjusting wheel 22. The holding foot 53 is fitted onto a plug connecting portion of the base portion 16 and provided with a retaining device 54 by which an end portion of a respiratory gas conduit, which is coupled to the breathing hose connecting portion 48, is additionally fixed. The forehead pads 49 that bear against the forehead of the mask user are displaceably mounted to the respective arm element 14, 15.

Figure 7:
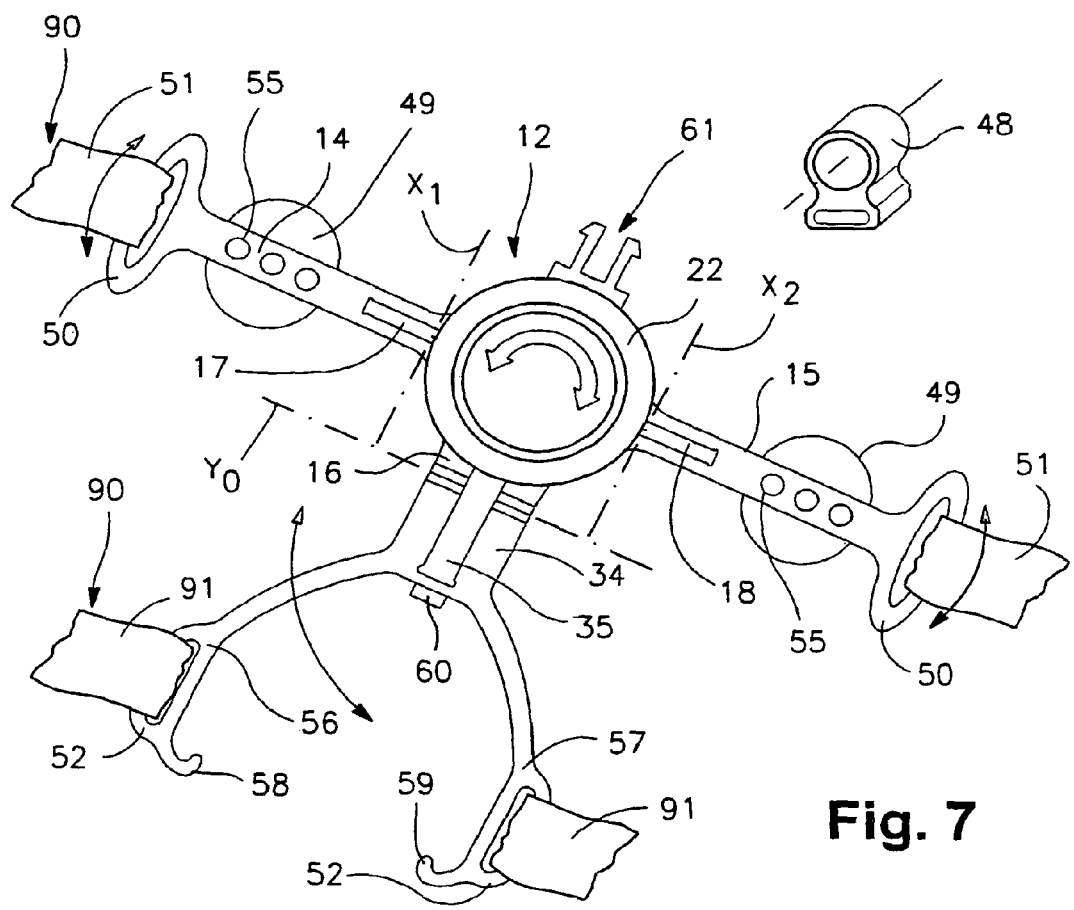
FIG. 7 shows a perspective view of an embodiment of an application device having an integrated forehead support device for the application of a breathing mask.

FIG. 7 shows an embodiment of an application device for a breathing mask, in which the left arm element 14, the right arm element 15 and the holding portion 34 can be tilted about the axes $X_1$, $X_2$ and $Y_0$ respectively in a defined manner by way of the adjusting drive 12 which is actuable by an adjusting wheel 22. The tilting movement of those components is effected in each case by way of the coupling members 17, 18 and 35 which are associated with those parts. Support for the arm elements 14, 15 against the forehead region of a mask user is by way of the forehead pads 49 which have already been referred to with reference to FIG. 6 and which in this embodiment can be inserted into insert openings 55 provided on the respective arm elements 14 and 15. The arm elements 14, 15 are each provided with the respective eye portion 50 through which a portion of the upper headband arrangement 51 of the headband assembly 90 can be passed.

In the illustrated embodiment, the holding portion 34 is made from a high-strength plastic material, e.g., polyamide, and is of a frame-like configuration. However, the holding portion 34 may be made from any other suitable material. The holding portion 34 includes two holding arms 56, 57 which are each provided with a respective eye portion 52 through which an end portion of the lower headband arrangement 91 of the headband assembly 90 can be passed.

The holding arms 56, 57 are provided with an engagement structure 58,59 by way of which the holding arms can be brought into engagement with a mask base body. Fixing of the mask base body in the holding portion 34 is further effected by a retaining or latching projection 60 which is formed, e.g., integrally with the holding portion 34. Provided on a side of the base portion 16, which is remote from the holding portion 34, is a push-on portion 61, onto which a breathing hose connecting portion can be fitted. The breathing hose connecting portion 48, as indicated in FIG. 6, can serve to conduct the respiratory gas into the interior of the mask, as is defined by a mask base body.

Figure 8:
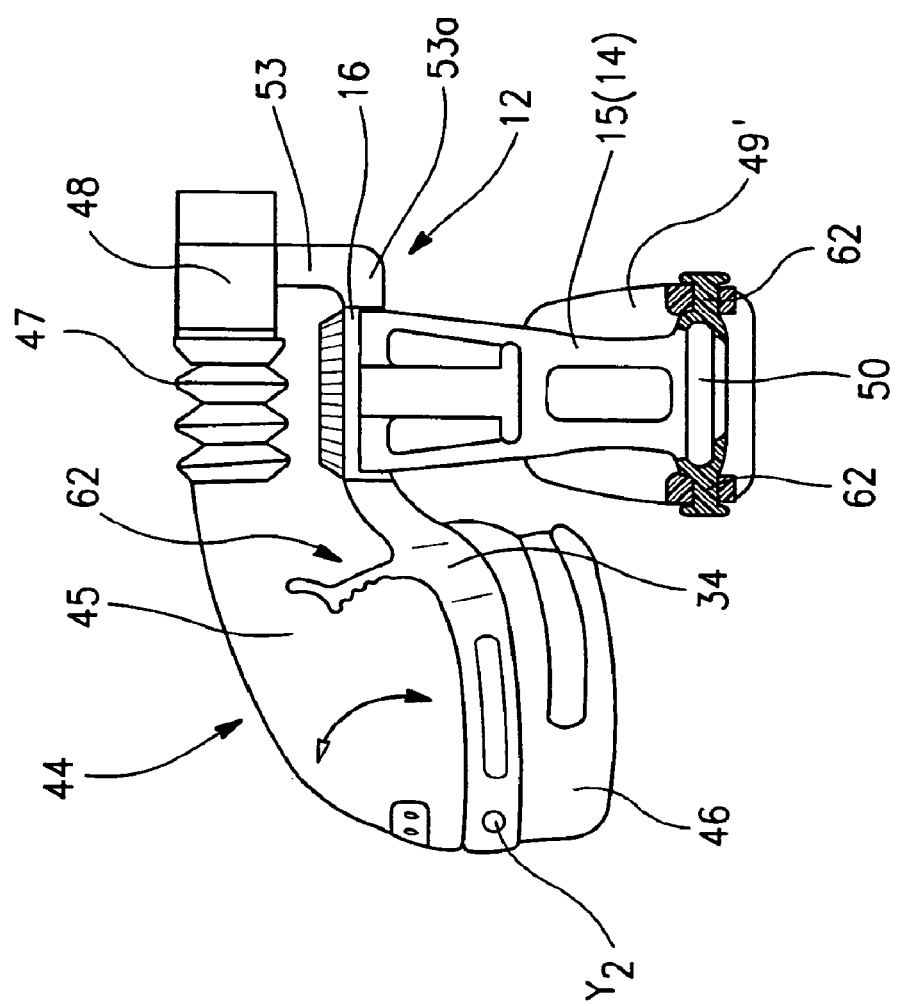
FIG. 8 shows a side view of an embodiment of a breathing mask application device having a breathing mask arrangement pivotably movably accommodated therein.

FIG. 8 shows an embodiment of an application device which is provided with a breathing mask arrangement 44 and which, similarly to the embodiments described hereinbefore, includes an adjusting drive 12, by way of which the arm elements 14, 15 which project on both sides from a base portion 16 of the adjusting drive 12, can be adjustably pivoted. As shown in FIG. 8, the mask base body 45 is tiltable, independently of the adjusting movement of the arm elements which is caused by the adjusting drive 12, about a pivot axis $Y_1$ which extends approximately in the region of the zone of the sealing lip device, which is adjacent to the nostrils of a mask user, and which extends substantially parallel to a transverse line 6 joining the eyebrows. The pivotal position of the mask base body 45 with respect to the holding portion 34 can be fixed by an arresting device 62. A sufficient relative mobility of the mask base body 45 with respect to a breathing hose connecting portion 48 provided for the connection of a respiratory gas conduit is achieved by a flexible conduit portion 47, as is provided also in the embodiment shown in FIG. 6. In this embodiment, the mask base body is produced in one piece with a sealing lip device 46 from a elastomer material, e.g., silicone rubber. The breathing hose connecting portion 48 in this embodiment is rigidly coupled to the base portion 16 and is made from a hard thermoplastic material, for example.

The arm elements 14, 15 include forehead pads 49' mounted thereto, as shown in FIG. 8, which are provided to bear against the surface of the forehead of the mask user, the forehead pads 49' being suspended tiltably on trunnions or projections 62 which are formed, e.g., integrally with the respective arm element 15, 14. Disposed between the trunnions 62 there is an eye portion 50 for passing therethrough an end portion of an upper band arrangement. The base portion 16 may be guided displaceably on an arm portion 53a which extends from the holding portion 34 to the holding foot 53. As a result, the vertical spacing of the forehead support device from the sealing lip device 46 may be variably altered.

FIG. 9 shows a further embodiment of the holding portion 34, as can be used for example in relation to the embodiments shown in FIGS. 7 and 8. In the illustrated embodiment, the holding portion 34 is provided with a coupling structure which is provided for coupling a mask base body (not shown). Thus, the mask base body can be coupled to the holding portion 34 in different coupling positions.

FIG. 10 shows an embodiment of a forehead support device which can be fitted by way of a breathing hose connecting portion 48 onto a connecting part 64 of a breathing mask.

In the illustrated embodiment, the breathing hose connecting portion 48 is coupled to a base portion 16 of the forehead support device 16 by way of a holding foot 53. By way of an adjusting wheel 22 arranged between the breathing hose connecting portion 48 and the base portion 16, the coupling members 17, 18 may be adjustably moved in a direction radially with respect to the axis of rotation 24 of the adjusting wheel 22. The arm elements 14, 15 may be pivoted about the axes $X_1$, $X_2$ by suitable positioning of the coupling members 17, 18.

As shown in FIG. 10, the arm elements 14, 15 include forehead contact pads 49 mounted thereto by way of which the arm elements 14, 15 are supported on the forehead region of a mask user. Provided in the region of the forehead pads 49 on the arm elements 14, 15 are eye portions 50 through which the respective end portion of an upper belt arrangement can be passed.

It can thus be appreciated that the aspects of the present invention have been fully and effectively accomplished. The foregoing specific embodiments have been provided to illustrate the structural and functional principles of the present invention, and are not intended to be limiting. To the contrary, the present invention is intended to encompass all modifications, alterations, and substitutions within the spirit and scope of the detailed description.

What is claimed is:

1. An application device for a breathing mask arrangement, comprising:
 a headband assembly including an upper headband arrangement and a lower headband arrangement;
 a forehead support device including:
  a base portion;
  a right arm element pivotally mounted to the base portion for pivotal movement about a first pivot axis, the right arm having an end portion connected to the upper headband arrangement; and
  a left arm element pivotally mounted to the base portion for pivotal movement about a second pivot axis, the left arm having an end portion connected to the upper headband arrangement;
  the right and left arm elements each provided with a contact portion for bearing against a right and a left forehead zone respectively of a mask user;
  a holding portion structured to support the breathing mask arrangement and pivotally mounted to the base portion for pivotal movement about a third pivot axis, the holding portion including a pair of holding arms structured to connect to the lower headband arrangement; and
 an adjusting drive device structured to pivot the holding portion about its third pivot axis and the right and left arm elements about its respective first and second pivot axes into a predetermined pivot position;
 wherein the first and second pivot axes are spaced apart and substantially parallel to one another and the third pivot axis is adapted to extend substantially transverse to the first and second pivot axes.

2. A breathing mask arrangement, comprising:
 a breathing mask main body;
 a sealing lip structure coupled to said main body to define a compartment for breathing gas transfer in cooperation with a user's face; and
 a forehead support structure intended to support said main body within a mask user's forehead area, the forehead support structure including:
  a right arm element;
  a left arm element,
  both said arm elements being capable to pivot relative to said main body;
  a left forehead support pad including a left pad mounting structure pivotally mounted to a left pivot shaft provided by the left arm and structured to allow pivotal movement of the left forehead support pad with respect to the left arm in use about a pivot axis defined by the left pivot shaft; and
  a right forehead support pad including a right pad mounting structure pivotally mounted to a right pivot shaft provided by the right arm and structured to allow pivotal movement of the right forehead support pad with respect to the right arm in use about a pivot axis defined by the right pivot shaft,
  said left and right support pads being structured to provide a plate-shaped contact area intended to bear against the forehead of the mask user.

3. A breathing mask arrangement, comprising:
 a breathing mask main body defining a mask interior breathing chamber structured to accommodate the patient's nose;
 a sealing lip structure structured to form a seal with a user's face, the main body and sealing lip structure formed in one piece from an elastomeric material;
 a forehead support structure intended to support said main body within a mask user's forehead area, the forehead support structure including:
  a right arm element; and
  a left arm element,
  both said arm elements being capable to pivot relative to said main body;
  an adjusting drive device structured to effect pivotal movement of the right and left arm elements relative to the main body into a predetermined pivot position; and
 a breathing gas conduit connector made from rigid material,
 wherein said main body forms a conduit opening structured to connect with said breathing gas conduit connector.

4. A breathing mask arrangement according to claim 2, further comprising a rotatable adjusting wheel associated with the right and left arm elements such that rotative movement of the adjusting wheel is adapted to cause relative movement between the right and left arm elements and the main body.

5. A breathing mask arrangement according to claim 2, wherein the mask main body is tiltable independently of the pivotal movement of the arm elements.

6. A breathing mask arrangement according to claim 3, wherein the main body includes a flexible conduit portion in the form of a bellows structure that is adapted to connect to breathing gas conduit connector.

7. A forehead support for a breathing mask, comprising:
   a base portion;
   a right arm element pivotally mounted to the base portion for pivotal movement about a first pivot axis;
   a left arm element pivotally mounted to the base portion for pivotal movement about a second pivot axis spaced apart from the first pivot axis;
   a holding portion adapted to connect to the breathing mask and pivotally mounted to the base portion for pivotal movement about a third pivot axis; and
   an adjusting drive device structured to pivot the holding portion about its third pivot axis and the right and left arm elements about its respective first and second pivot axes into a predetermined pivot position;
   wherein the right and left arm elements are arranged such that in use the first and second pivot axes are substantially parallel to one another and the holding portion is arranged such that in use the third pivot axis is adapted to extend substantially transverse to the first and second pivot axes.

8. A forehead support according to claim 7, wherein the adjusting drive device includes a rotatable adjustment knob.

9. A forehead support according to claim 7, wherein the first, second, and third pivot axes are defined by hinge devices.

10. A forehead support according to claim 7, wherein each arm element includes a forehead pad adapted to contact the forehead region of the mask user in use.

11. A forehead support according to claim 10, wherein the forehead pad is selectively inserted into one of multiple insert openings provided in each arm element.

12. A breathing mask arrangement, comprising:
   a headband assembly including an upper headband arrangement and a lower headband arrangement;
   a mask base body including a mask interior breathing chamber;
   a sealing lip device provided to the mask base body and adapted to form a seal with a user's face;
   a forehead support device including:
      a base portion;
      a right arm element provided to the base portion, the right arm element having an end portion connected to the upper headband arrangement;
      a left arm element provided to the base portion, the left arm element having an end portion connected to the upper headband arrangement;
      a holding portion interconnecting the mask base body and the base portion; and
      a finger-operated adjusting wheel rotatably supported on the base portion and manually manipulable to adjust a position of the right and left arm elements;
   a breathing gas conduit connector provided to the mask base body, the breathing gas conduit connector being more rigid than the mask base body; and
   a forehead pad supported by the forehead support device and adapted to bear against the user's forehead, the forehead pad being tiltably suspended for pivotal movement about a pivot axis, and a forehead pad connecting device including a pad mounting structure pivotally mounted to a pivot shaft to allow the pivotal movement between the forehead pad and the forehead support device.

13. A breathing mask arrangement according to claim 12, wherein the adjusting wheel is oriented towards an upper portion of the mask base body.

14. A breathing mask arrangement according to claim 13, wherein the right and left arm elements are movable simultaneously by the adjusting wheel.

15. A breathing mask arrangement according to claim 14, wherein the adjusting wheel includes a fluted or grooved structure along its outside peripheral region.

16. A breathing mask arrangement, comprising:
   a headband assembly including an upper headband arrangement and a lower headband arrangement;
   a frame;
   a sealing structure supported by the frame and adapted to form a seal with a user's face;
   a breathing gas conduit connector provided to the frame;
   a forehead support device pivotally connected to the frame, including:
      a base portion pivotally connected to the frame for pivotal movement about a pivot axis;
      a right arm element provided to the base portion, the right arm element having an end portion connected to the upper headband arrangement;
      a left arm element provided to the base portion, the left arm element having an end portion connected to the upper headband arrangement;
      a finger-operated adjusting structure manually manipulable to effect pivotal movement of the forehead support device;
   wherein the right and left arm elements include an included angle where they intersect, as seen in front view of the patient's face in use, of less than 180°.

17. A breathing mask arrangement according to claim 16, wherein the forehead support device supports at least one forehead pad.

18. A breathing mask arrangement according to claim 17, wherein each arm element supports a distinct forehead pad.

19. A breathing mask arrangement according to claim 18, wherein the right and left arm elements include a general "Y" shape when viewed from the front of the patient's face in use.

* * * * *